United States Patent
Yin et al.

(10) Patent No.: US 11,951,171 B2
(45) Date of Patent: Apr. 9, 2024

(54) POLYPEPTIDE EXP AND ITS DRUG DELIVERY SYSTEM AS WELL AS EXTRACELLULAR VESICLE EXTRACTION

(71) Applicant: TIANJIN MEDICAL UNIVERSITY, Tianjin (CN)

(72) Inventors: Haifang Yin, Tianjin (CN); Ning Ran, Tianjin (CN); Caorui Lin, Tianjin (CN); Xianjun Gao, Tianjin (CN)

(73) Assignee: TIANJIN MEDICAL UNIVERSITY, Tianjin (CN)

( * ) Notice: Subject to any disclaimer, the term of this patent is extended or adjusted under 35 U.S.C. 154(b) by 619 days.

(21) Appl. No.: 17/053,244

(22) PCT Filed: Dec. 18, 2019

(86) PCT No.: PCT/CN2019/126161
§ 371 (c)(1),
(2) Date: Nov. 5, 2020

(87) PCT Pub. No.: WO2021/088214
PCT Pub. Date: May 14, 2021

(65) Prior Publication Data
US 2022/0211856 A1  Jul. 7, 2022

(30) Foreign Application Priority Data
Nov. 8, 2019 (CN) .......................... 201911084784.X

(51) Int. Cl.
*A61K 47/64* (2017.01)
*C07K 7/08* (2006.01)
*C12N 5/00* (2006.01)
*C12N 5/078* (2010.01)

(52) U.S. Cl.
CPC ................ *A61K 47/64* (2017.08); *C07K 7/08* (2013.01); *C12N 5/0634* (2013.01); *C12N 2509/00* (2013.01)

(58) Field of Classification Search
CPC ......... A61K 47/64; C07K 7/08; C12N 5/0634
See application file for complete search history.

(56) References Cited

U.S. PATENT DOCUMENTS

| 10,253,327 | B2 * | 4/2019 | Matarasso | .......... C12N 15/8271 |
| 2004/0214272 | A1 * | 10/2004 | La Rosa | ............ C12N 15/8242 800/278 |
| 2015/0106973 | A1 * | 4/2015 | Matarasso | .......... C12N 15/8261 800/278 |

FOREIGN PATENT DOCUMENTS

| CN | 105111283 A | 12/2015 |
| CN | 106661086 A | 5/2017 |

* cited by examiner

*Primary Examiner* — Amber D Steele
(74) *Attorney, Agent, or Firm* — Stuart H. Mayer; Kaplan Breyer Schwarz LLP

(57) ABSTRACT

The present invention "A polypeptide EXP and its drug delivery system as well as extracellular vesicle extraction kit thereof" belongs to the field of biomedical engineering and diagnostics. The amino acid sequence of the polypeptide EXP is set forth in SEQ ID NO. 1. Based on the polypeptide EXP, the present invention also provides a drug delivery system, targeted drug delivery system, enhanced drug delivery vehicle, a drug with enhanced delivery, targeted drug, extracellular vesicle extraction kit, disease diagnostic kit, a method for purifying extracellular vesicles, and use of the polypeptide EXP in pharmacy and diagnostic reagent manufacture.

26 Claims, 6 Drawing Sheets
(6 of 6 Drawing Sheet(s) Filed in Color)
Specification includes a Sequence Listing.

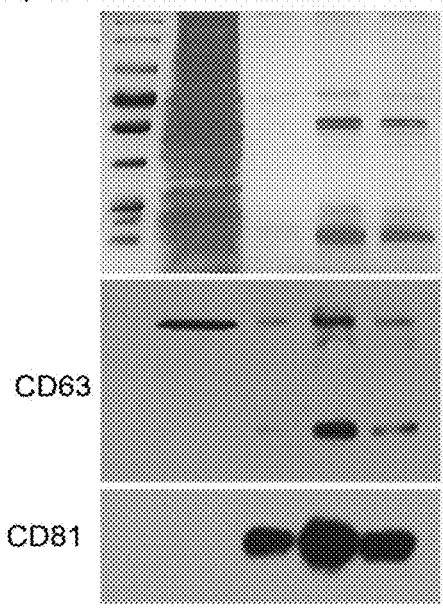
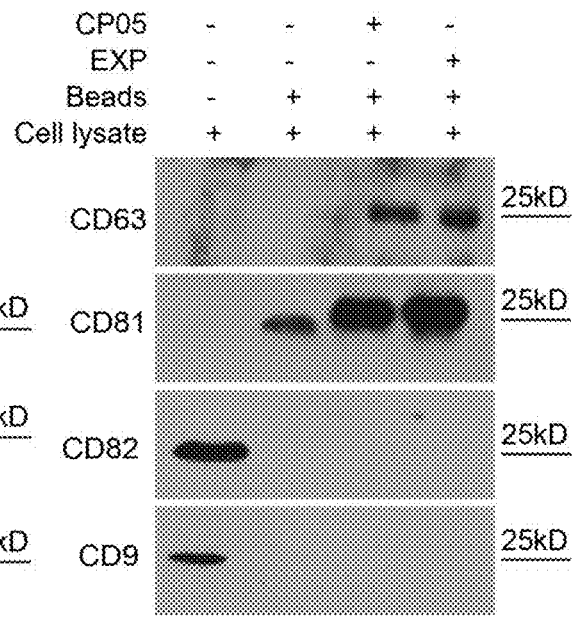
Figure 4
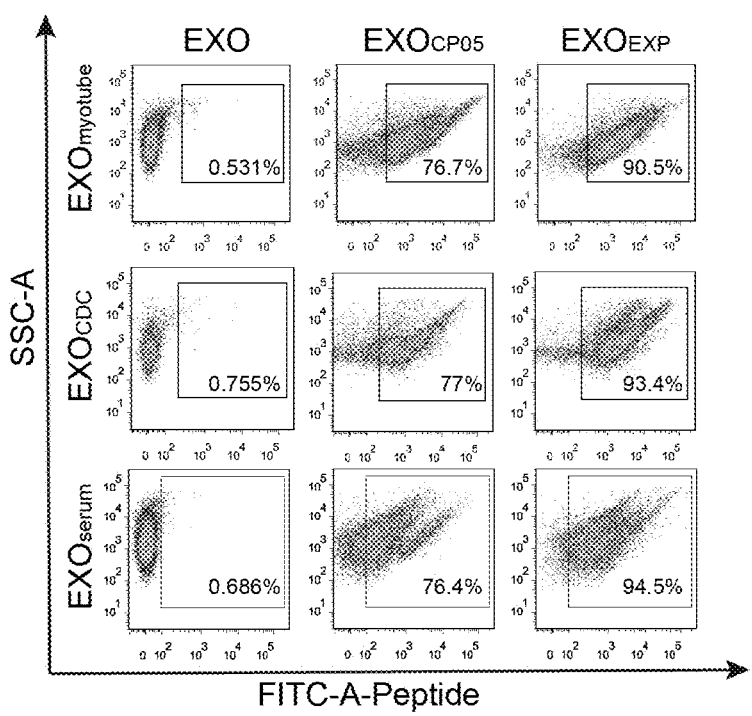
Figure 5

POLYPEPTIDE EXP AND ITS DRUG DELIVERY SYSTEM AS WELL AS EXTRACELLULAR VESICLE EXTRACTION

CROSS REFERENCE TO RELATED APPLICATION

This application is a National Phase in the United States of PCT/CN2019/126161, filed Dec. 18, 2019, which claims priority to Chinese Application No. 201911084784.X, filed Nov. 8, 2019, the contents of which are incorporated herein by reference.

TECHNICAL FIELD

The present invention relates to the field of biomedical engineering, in particular to a polypeptide EXP and its drug delivery system as well as extracellular vesicle extraction kit thereof.

BACKGROUND ART

Extracellular vesicles (EVs) are vesicles with lipid bilayer structure, which are secreted by various cells and released into the extracellular space. The EVs can be classified as two types: exosome and Microvesicles (MV). Extracellular vesicles play an important role in biological processes such as information transmission and material exchange among cells.

Exosomes are a kind of biological vesicles with a diameter of 30-150 nm, which are widely distributed in cell supernatant, blood, urine and other sources, etc. Exosome can carry endogenous protein, mRNA, miRNA, and non-coding RNA, which mediate the material exchange, signal transmission and antigen presentation among cells, during formation process. At the same time, exosome, as nano lipid vesicle secreted by cell, have the advantages of high histocompatibility and low immunogenicity compared with other nano liposomes. Therefore, exosomes can be used as natural biological nanovector and show great potential for the use in drug delivery.

Exosomes have been used as vectors of endogenous proteins, nucleic acids and other biological molecules for disease diagnosis and treatment. However, there are limited studies on the surface functionalization of exosomes. Previous studies focused on using recombinant plasmids to fuse the target protein with the membrane protein source cells on the surface of exosomes, and collect the exosomes secreted by the source cells to achieve surface modification of exosomes. However, due to the low efficiency of plasmid transfection, unclear conformation of targeting peptide fusion expression and low recovery efficiency of exosomes, the application of exosomes as natural biological nano vectors has been hindered. Therefore, development of a new method of surface functionalization of exosomes to improve the multi-loading efficiency of exosomes as drug delivery vectors is of great significance for the clinical application of exosomes. Extracellular vesicles, secreted by cells, are mainly membrane vesicle structure formed by cell membrane shedding, with a diameter of 150-1000 nm, which can also carry protein and RNA from source cells for material exchange and information transmission among cells. At the same time, the lipid membrane structure determines that it can be used as a vector of substance transport for drug delivery like exosomes. Therefore, it is imperative to develop a method that can modify the surface of exosome and macrovesicle to improve the loading efficiency of drug delivery.

The prior art, a Chinese patent NO. CN201510520565.7 provides a polypeptide CP05 with specific binding ability to CD63 on exosome surface, and binds the specific targeting peptide, functional peptide and nucleic acid drug to the surface of exosomes, so as to achieve surface modification of exosomes via CP05. The feasibility of CP05 as an anchor peptide is confirmed by functional tests in vitro and in vivo experiments. However, the binding efficiency of CP05 to exosomes is limited, and the CP05 did not bind to or extremely inefficiently bind to exosome that did not express or express low level of CD63.

SUMMARY OF THE INVENTION

Based on above defects and deficiencies in the field, the invention develops and obtains a new polypeptide which is named as EXP (Extracellular vesicle binding peptide). Compared to CP05, the binding efficiency of EXP with exosomes is about 2 times higher than that of CP05 under the same conditions; especially, the binding efficiency of EXP to exosomes from serum is significantly higher than that of CP05, and the binding capacity with exosomes is stronger. EXP can be used for the extraction of serum exosomes, and the extraction rate is about 2 times higher than that of CP05. The present invention provides a more efficient polypeptide for the surface functionalization and extraction of exosomes.

The technical solution of the present invention is as follows:

A polypeptide EXP, characterized in that, its amino acid sequence is shown as SEQ ID NO.1.

A drug delivery system, characterized in that, comprises the polypeptide EXP according to claim 1 and drug delivery vector.

Said polypeptide EXP binds to drug delivery vectors via CD63 and/or CD81 protein;

Preferably, the drug delivery vector is vector that can express or carry CD63 and/or CD81; the vector can express or carry CD63 and/or CD81 is selected from exosome, extracellular microvesicle, exosome, extracellular microvesicle expressing or attaching CD63 and/or CD81 protein, liposome, nanoparticle.

The drug delivery systems also comprises pharmacodynamically active molecule;

Said pharmacodynamically active molecule are selected from polypeptide, nucleic acid, and small molecular compound which can be covalently conjugated to EXP;

Preferably, the polypeptide that can be covalently conjugated to EXP is selected from muscle-targeting peptide M12, liver cancer-targeting peptide P47, cranial nerve-targeting peptide RVG and other functional polypeptides, for example, N1ND;

Preferably, the small molecule compound is selected from Phosphorodiamidate Morpholino Oligomer (PMO);

Preferably, the nucleic acid which can be covalently conjugated to EXP is selected from neutral and uncharged PMO or PNA.

The polypeptide that can be covalently linked with EXP can also be a targeting peptide targeting different tissues, or a functional polypeptide of any sequence. Since polypeptide synthesis is a very mature technology, EXP is also a kind of polypeptide, which can be artificially synthesized with any other polypeptide, and any polypeptide can be synthesized with EXP, which is also the advantage of EXP. It's available to synthesize EXP with any sequence of peptide through mature peptide synthesis technology.

A targeted drug delivery system, characterized in that, comprises the polypeptide EXP, drug delivery vector and targeting peptide.

The polypeptide EXP binds to drug delivery vector via CD63 and/or CD81 site;

Preferably, the drug delivery vector is vector that can express or carry CD63 and/or CD81; the vector that can express or carry CD63 and/or CD81 is selected from exosome, extracellular microvesicle, exosome, extracellular microvesicle attaching CD63 and/or CD81 protein, liposome, nanoparticle.

The targeted drug delivery system also comprises pharmacodynamically active molecule; said pharmacodynamically active molecule is selected from polypeptide and nucleic acid which can be covalently conjugated to EXP;

Preferably, said polypeptide which can be covalently conjugated to EXP is selected from M12, P47, RVG or N1ND;

Preferably, said nucleic acid that can be covalently conjugated to EXP is selected from PMO.

An enhanced drug delivery vector, characterized in that, is a drug delivery vector which it linked or modified by the polypeptide EXP.

Said polypeptide EXP binds to the drug delivery vector via CD63 and/or CD81 site;

Preferably, the drug delivery vector is vector that can express or carry CD63 and/or CD81; the vector that can express or carry CD63 and/or CD81 is selected from exosome, extracellular microvesicle, plasmid that can express CD63 and/or CD81.

A transport enhanced drug, characterized in that, the effective component of the drug is loaded on the enhanced drug delivery vector.

For example, HMGN1, a specific polypeptide drug, its nucleotide sequence and EXP nucleic acid sequence can be loaded into gene expression vector (e.g. lentiviral expression vector pCDH-CMVpuro-insulin-HMGN1 vector). The peptide sequence of HMGN1+EXP can be expressed by the gene expression vector, and then the structure of HMGN1+EXP+drug delivery vector can be formed by the combination of EXP and CD63 and/or CD81 on drug delivery vector, that is, a transport enhanced drug of polypeptide is obtained.

For polypeptide shorter than 60 amino acids, no gene expression system is needed; for polypeptide or protein larger than 60 amino acids, gene expression vector is needed.

In other embodiments, nucleic acid drug PMO can be covalently conjugated with EXP to obtain a complex structure of PMO-EXP, subsequently PMO-EXP binds to CD63 and/or CD81 on drug delivery vector via EXP to generate a structure of PMO-EXP-drug delivery vector, namely a transport enhanced drug of nucleic acid.

A targeted drug, characterized in that, the drug composition of the targeted drug is included in the targeted drug delivery system.

For example, PMO covalently conjugated to EXP can be used in the treatment of DMD.

An extracellular vesicle extraction kit, characterized in that, comprises the polypeptide EXP.

The extracellular vesicle kit also comprises reagent for isolating and purifying extracellular vesicle;

Preferably, said reagent for isolating and purifying extracellular vesicle includes:

More preferably, said polypeptide EXP is coated on nickel bead, or magnetic bead, or covalently linked to microsphere or nanobead by mature chemical processing.

The extracellular vesicle is selected from exosome and/or microvesicle.

A disease diagnostic kit, characterized in that, the disease diagnosis marker is exosomes surface protein molecule, disease-related specific protein molecule, for example liver cancer-specific antigen AFP; the kit includes the polypeptide EXP.

For example, as to diagnosing tumor patient or muscle patient, like CP05 of the prior art, the EXP can be attached to the magnetic bead to combine with free exosome, and the disease can be diagnosed by detecting the concentration of the bound exosomes.

The disease diagnostic kit also includes reagent for isolating and purifying exosome;

Preferably, the reagent for purifying exosome includes: EXP-coated nickel bead, binding solution (50 mM imidazole, 500 mM sodium chloride, 20 mM disodium hydrogen phosphate, pH 7.4), washing buffer (75 mM imidazole, 500 mM sodium chloride, 20 mM disodium hydrogen phosphate, pH 7.4); eluent buffer (500 mM imidazole, 500 mM sodium chloride, 20 mM disodium hydrogen phosphate, pH 7.4); all above reagents are commercially available.

Preferably, the exosome is selected from exosome from human serum, and/or, exosome from human urine, and/or, free exosome from other sources, and/or, exosome in cell culture supernatant.

A method for isolating and purifying extracellular vesicle, characterized in that, comprises binding or capturing the extracellular vesicle with the polypeptide EXP.

The method for purifying microvesicle also includes:
Step 1: His labeled EXP and CP05 (100 μg) are combined with 40 μl nickel bead in 200 μl binding solution, and incubated for 1 h at 4° C.;
Step 2: 1 mL of pre-centrifuged serum (4400 g, centrifugated for 20 min; 13000 g centrifugated for 5 min) is added to the nickel bead coated with His-EXP and His-CP05, and incubated at 4° C. for 30 min;
Step 3: discarding the serum and washing off non-specific binding with the washing buffer for 3 times with 10 min each time).
Step 4: eluting by 100 μl elution buffer to recover the extracellular vesicles.

The extracellular vesicle is selected from exosome and/or microvesicle.

The present invention also provides a use of the polypeptide EXP in pharmacy.

The use includes that the polypeptide EXP is connected with the drug delivery vector to obtain an enhanced drug delivery vector based on the EXP-vector complex.

Said use also includes: the drug molecule is connected with the EXP-vector complex to obtain a drug based on the drug molecule-EXP-vector complex.

Said use also includes: the targeting peptide is further connected with the drug molecule-EXP-vector complex to obtain targeted drug.

Use of the polypeptide EXP in preparation of disease diagnosis reagent.

Said use includes: the polypeptide EXP is connected with the exosomes.

Said exosome is derived from human serum, human urine, or other source.

The lipid bilayer structure of natural exosome can encapsulate drug molecule, and some exosome has tissue tropism, thus realizing drug targeted delivery, the EXP of the invention can effectively combine with exosome, and the binding efficiency of drug molecule and exosome can be improved by connecting drug molecule with EXP. In the present invention, drug molecule is linked to the external surface of exosome through EXP, which can deliver drug molecule to target cell by passive targeting of some exosome. On the other hand, if exosome is further linked to targeted peptide, the passive targeting of exosome will be changed by targeting peptide. At this time, targeted peptide plays a major role in targeting to deliver drug molecule to target cell.

The present invention provides a polypeptide EXP and related complex formed by the connection of the EXP. Wherein the amino acid sequence of the EXP is CRHKMWTVKSRL. Said polypeptide EXP can be linked to transmembrane protein on the surface of the vector by co-incubating with the vector The transmembrane protein linked with the polypeptide EXP involves transmembrane protein CD63 on surface of exosome and other transmembrane protein including CD81. The polypeptide EXP can be used for the surface functionalization of extracellular vesicle including targeted modification, drug loading, and capture of extracellular vesicle, which is used for clinical disease diagnosis.

The present invention obtained a polypeptide EXP which can bind to extracellular vesicle with a higher binding efficiency, and its sequence is CRHKMWTVKSRL. The EXP can binds to the transmembrane protein CD63 and CD81 on the surface of extracellular vesicle. Compared to the previous peptide CP05, EXP shows more efficient binding to exosomes. Said polypeptide EXP can be used for high-efficient capture of extracellular vesicle. and covalently combining with other functional molecule, such as targeted peptide, nucleic acid drug, to connect functional molecules on the surface of extracellular vesicle and realize the functionalization of extracellular vesicle. Said polypeptide EXP in the present invention overcomes the disadvantages in process of traditional exosome modification like low transfection efficiency with plasmid and low recovery efficiency of exosome encountered in the process of, and thus provides an efficient and convenient method for exosome surface modification. Meanwhile, the delivery complex obtained by said modification method is relatively stable and thus shows a expansive prospect in clinical use.

It's proven by experiments in the present invention that said polypeptide EXP can be used to load drug on extracellular vesicle, and can improve the loading efficiency of drug, whose main mechanism is that EXP can bind to CD63 and/or CD81 on the surface of extracellular vesicle, and thus facilitate the EXP-conjugated drug loaded on extracellular vesicle. EXP can extract extracellular vesicle in serum, and can bind to extracellular vesicle from different source. In a summary, the development of said polypeptide EXP provides a high-efficient approach for extracellular vesicles capture and surface functionalization, and the delivery complex composed of said polypeptide EXP shows a higher stability, which will accelerate the transformation of extracellular vesicle in clinical use.

DESCRIPTION OF DRAWINGS

The patent or application file contains at least one drawing executed in color. Copies of this patent or patent application publication with color drawing(s) will be provided by the Office upon request and payment of the necessary fee.

Each sign in the figure represents the detection results of the following sequences: EXO represents exosomes derived from murine myotubes; CP05 represents the polypeptide which is recorded in the prior art Chinese patent No. CN201510520565.7; EXP represents the polypeptide of the present invention (SEQ ID NO.1). 39880 and 399881 respectively represent two other variants of CP05. (A) Flow cytometry to detected the binding efficiency of different peptides with exosomes. It's shown by the results that EXP demonstrated the highest binding efficiency to exosomes, up to 95.5%, indicating the strongest binding capacity. (B) Flow cytometry to detected the capacity to enter cells of different peptides mediated by exosome. The equivalent amount FAM-labeled polypeptides were incubated with exosome derived from dC2C12 and added into C2C12 cells, and the capacity of enter cells was detected 24 hours later. It's shown by the results that 65.6% of EXO-EXP entered cells whose capacity is highest. (C) Quantitative analysis of different peptides entering cells mediated by exosome. It's shown by the results that the ratio of EXO-EXP positive C2C12 cells is highest, which is twice as mush as EXOCP05, which points out that the capacity of EXP enter cells mediated by EXO is higher than CP05 and other variants, and suggests that EXP bears stronger binding ability to exosomes than CP05. (D) the binding efficiency of different amount gradients of CP05 and EXP to the equivalent amount of exosomes was detected by Flow cytometry to. Different amounts of EXP and CP05(0.03 µg, 0.06 g, 0.3 µg) were co-incubated with exosomes (10 µg), and their binding efficiency was compared by flow cytometry. It's shown by the results that under different amount gradients, the binding efficiencies of EXP and exosome are all higher than that of CP05, and EXP exhibited a higher binding advantage particularly at low concentration.

FIG. 1A shows a flow cytometry to detected the binding efficiency of different peptides with exosomes.

FIG. 1B shows a flow cytometry to detected the capacity to enter cells of different peptides mediated by exosome.

FIG. 1C shows a quantitative analysis of different peptides entering cells mediated by exosome.

FIG. 1D shows the binding efficiency of different amount gradients of CP05 and EXP to the equivalent amount of exosomes was detected by Flow cytometryto.

Figure 2:
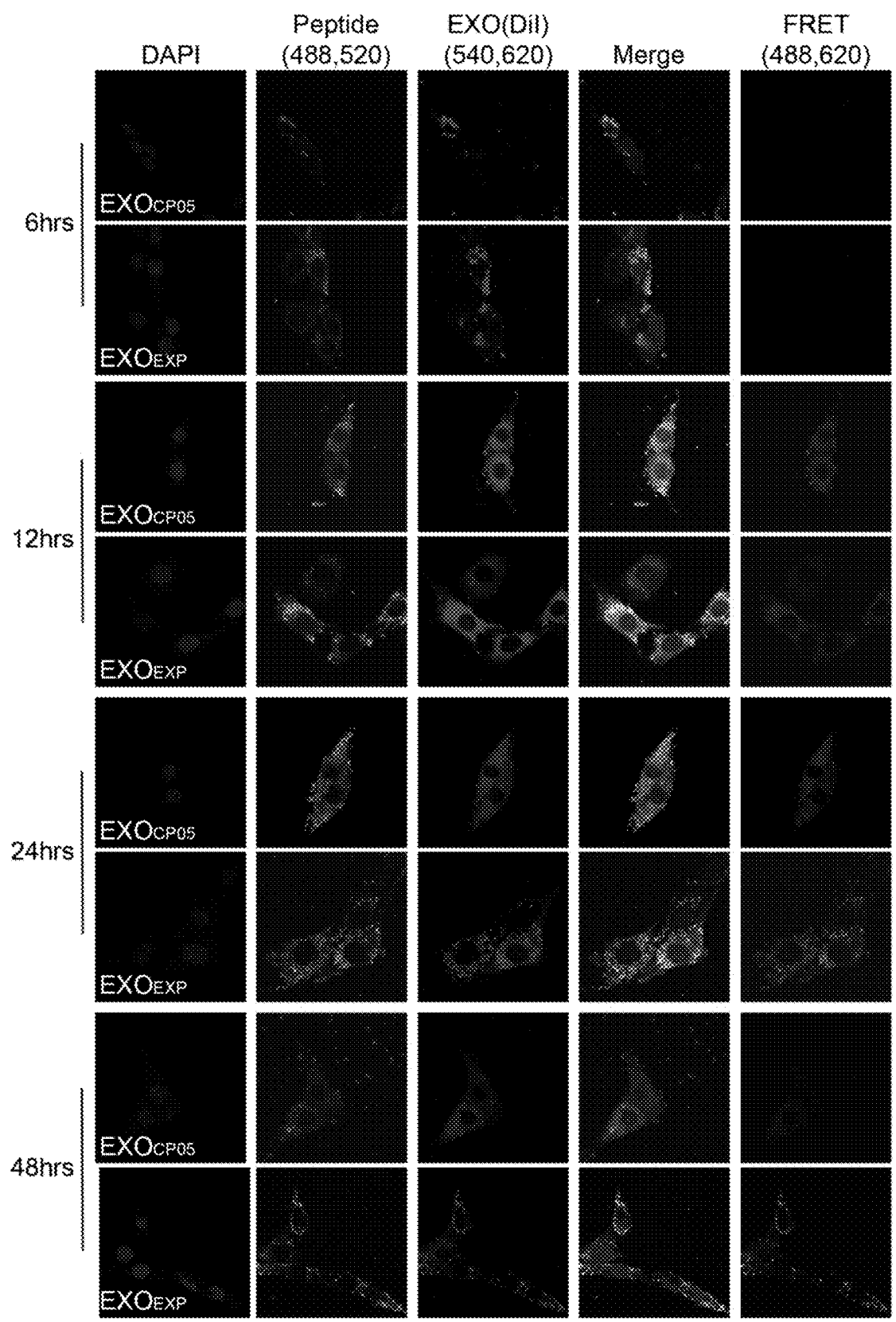

FIG. 2 shows the results for detecting the binding stability of CP05 and EXP with exosomes. The intracellular co-localization of CP05 and EXP with exosomes was examined with confocal microscopy at different timepoints. FAM-labeled CP05 and EXP were incubated with DiI-labeled exosomes and then added into C2C12 cells. The co-localization of peptides and exosomes were observed with confocal microscopy, and FRET was used to examine the binding capacity of peptides to exosomes at different timepoints (6 hours, 12 hours, 24 hours, 48 hours).

The meanings of the signs in the figure are as follows: DAPI means staining result for nuclei by DAPI, Peptide (488,520) refers to the excitation and emission wavelength of FAM-labeled CP05 and EXP; EXO(DiI)(540,620) refers to the excitation and emission wavelength for DiI-labeled exosomes; Merge is the superposition of above three staining results; FRET means fluorescence resonance energy transfer. Optical energy resonance transfer is an energy transfer phenomenon between two fluorescent molecules that are very close to each other. When the emission spectrum of the donor fluorescent molecule overlaps with the absorption spectrum of the acceptor fluorescent molecule, and the distance between two molecules is within the range of 10 nm, a non-radioactive energy transfer occurs. In the figure, the FAM-Peptide is the donor fluorescent molecule and DiI-EXO is the acceptor fluorescent molecule. FRET (488, 620) represents the excitation of FAM-Peptide and the absorption wavelength of DiI-EXO. EXOCP05 is the staining result of exosomes combined with CP05 sequence which is recorded in the prior art Chinese Patent No. CN201510520565.7, and EXOEXP refers to the staining result of the combination of EXP of the present invention and exosomes. It's shown by the results that there was co-localization between EXP and CP05 with exosomes in cells at different timepoints. The co-localization of CP05 and EXO in the cells reached the peak in 12 hours, and reduced after 24 hours. Most of CP05 degraded at 48 hours, and the co-localization of CP05 and EXO was significantly reduced. However, as to EXP, the co-localization of EXP and EXO was still detectable in cells at 48 hours, which suggests a stronger binding stability of EXP with EXO than CP05.

Figure 3:
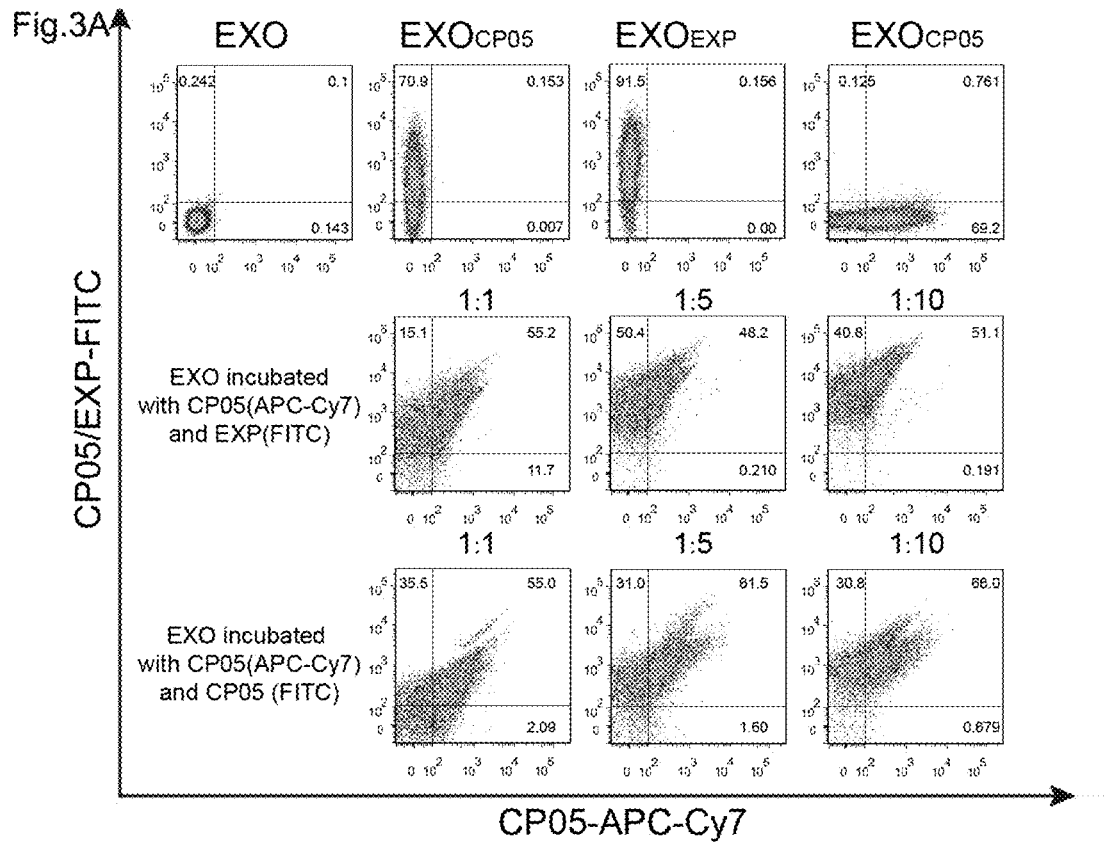

FIG. 3 shows the detecting results on the capacity of the competitive binding of CP05 and EXP to exosomes. AF750 (APC-Cy7)-labeled CP05 and FAM-labeled CP05 or EXP were co-incubated with exosomes at ratios of 1:1 or 1:5 (mass ratio), and the binding efficiency was detected with flow cytometry. It's shown by the results that when EXP and CP05 were incubated with exosomes at the same time, EXP could compete with CP05 to combine with exosomes, thus reducing the binding efficiency of CP05 and exosomes. (A) Flow cytometry to detect the binding efficiency of EXP or CP05 to exosomes. EXO was used as negative control; EXOCP05 is the binding efficiency of CP05 (FAM, af750) separately labeled by different fluorescence labeling with exosomes. EXOEXP is the binding efficiency of FAM labeled EXP andexosomes. 1:1, 1:5, 1:10 means different mass ratios of AF750 and FAM-EXP/FAM-CP05 are respectively as 1:1, 1:5, 1:10. It's shown by the results of flow cytometryto that the binding efficiency of CP05 alone with EXO was about 70%, while that of EXP and exosomes was 91.5% (flow cytometry to chart: the first line). When CP05 and EXP was co-incubated with exosome, it's discovered by detecting their binding efficiency that (flow cytometry to chart: the middle row), And the binding efficiency of EXOCP05(AF750) reduced after mass of EXP was increased to 5-fold and 10-fold higher than that of CP05. However, it's found by comparing different fluorescence CP05 molecules (flow cytometry to chart: the third line) that, the binding efficiency of EXOCP05 (AF750) remained unchanged with increasing the mass ratio of FAM-CP05. It is suggested that EXP can competitively bind the binding sites of CP05 and exosomes, resulting in the decrease of binding efficiency. (B) shows quantitative analysis of the binding efficiency of polypeptides to exosomes. Different fluorescence-labeled CP05 (APC-Cy7, FAM) were co-incubated with exosomes, their binding efficiency is detected with flow cytometry. CP05 (AF750) means the binding efficiency of wherein exosome with CP05(AF750). CP05 (FAM) means the binding efficiency of wherein exosome with CP05(FAM); EXP (FAM) means the binding efficiency of wherein exosome with EXP(FAM). It's indicated by the results (as shown in the first row of the table) that the binding efficiency of CP05(AF750) to exosomes remained the same (from 57% to 63.1%) when amounts of FAM-CP05 was increased after exosome and CP05(AF750) were co-incubated with CP05(FAM). However, after exosome and CP05 (AF750) were co-incubated with EXP(FAM) (the second row of the table), the binding efficiency of CP05(AF750) was decreased (from 66.9% to 48.4%) as amounts of FAM-EXP was increased.

FIG. 3A shows a flow cytometry to detect the binding efficiency of EXP or CP05 to exosomes.

FIG. 3B shows a quantitative analysis of the binding efficiency of polypeptides to exosomes.

FIG. 4 shows target detection of EXP. (A) Silver staining and Western blot were used to detect the interest proteins band obtained by co-immunoprecipitation. Flag-tagged CP05 or EXP was incubated with anti-flag coated beads, and followed by co-incubation with cell lysates after removing the free peptides which were unconjugated with beads. The specific enriched proteins in the cell protein lysate were fished by using the polypeptide. Then the size distribution of the fishing strip was detected by silver staining, and the expression of different Tetraspanin family proteins in the fishing strip was detected by Western blot. It's shown by the results that there were distinct protein bands with sizes of about 45 kD and 25 kD appeared in the EXP group in comparison to the control group. It's confirmed by the western blot results that these the distinct protein bands are CD63 and CD81. (B)Immunoprecipitation was used to catch the target of EXP. The results are the same as above.

FIG. 4A shows that silver staining and Western blot were used to detect the interest proteins band obtained by co-immunoprecipitation.

FIG. 4B shows that immunoprecipitation was used to catch the target of EXP.

FIG. 5 shows the results of detecting the binding ability of EXP to exosomes from different sources, and the binding efficiency of CP05 and EXP with exosomes from different sources detected by Flow cytometry. FAM-labeled CP05 or EXP was co-incubated with exosomes derived from murine myotubes(EXOmyotube), cardiac sphere cells (CDC) (EXOCDC) and human serum (EXOserum), and the binding efficiency was detected with flow cytometry. It's shown by the results that the binding efficiency of CP05 to exosomes from different sources is about 70%, and the binding efficiency of the same amount of EXP with exosomes from corresponding sources was about 90%. When incubated with exosomes from different sources, EXP showed higher binding efficiency.

Figure 6:
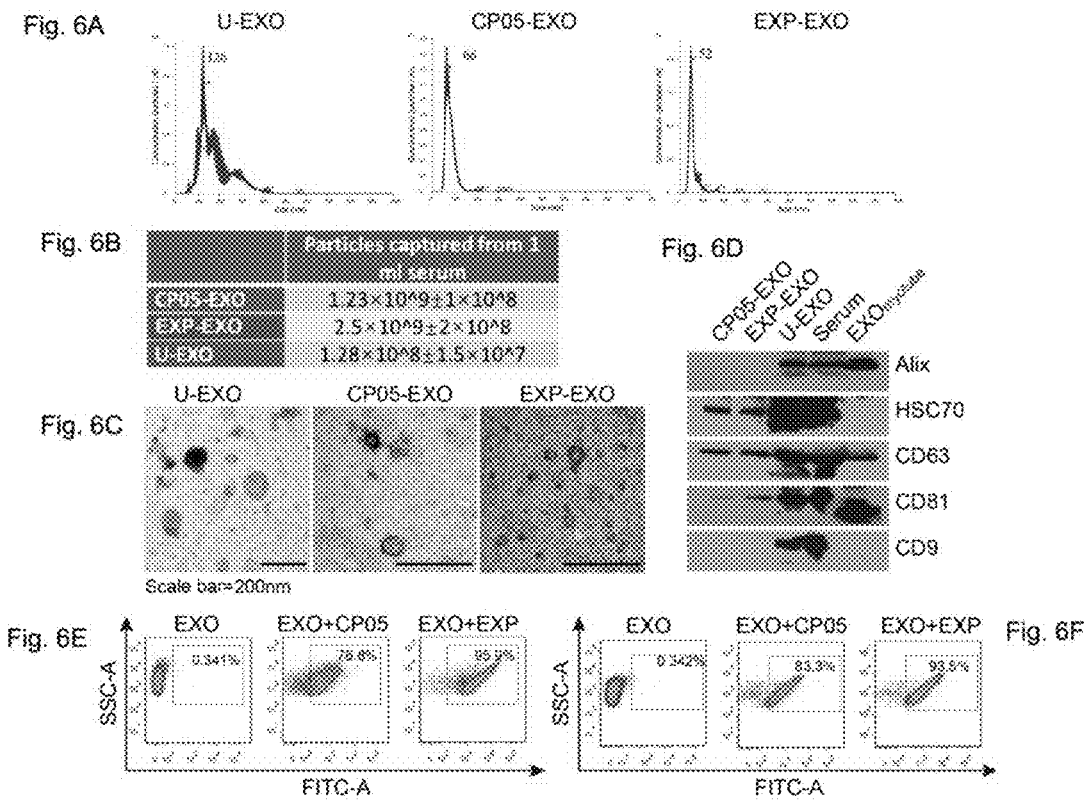

FIG. 6 shows exosomes morphology identification and application ability detection of exosomes in EXP captured serum. (A) Nano sight was used to detect the particle size of exosomes in serum captured by CP05 and EXP. It's shown by the results that the particle size of exosomes captured by EXP was about 50 nm, whose homogeneity was higher than that of exosomes recovered by ultra separation. (B) shows methods of CP05 and EXP capture and comparison of the number of exosomes in the equivalent ultra separated serum; (C) The morphology and size of exosomes captured by CP05 and EXP were detected by transmission electron microscopy. It's shown by the results that exosomes captured by EXP has typical bi-layer structure, and the size of exosomes captured by EXP was smaller than that of exosomes recovered by ultrafiltration.(D) Western blot was used to detect the marker protein capturing exosome. It's shown by the results that EXP captured marker proteins CD63, CD81 and HSC70 expressed by exosome.(E) The binding efficiency of exosomes in serum with CP05 and EXP was detected. It's shown by the results that: exosomes recovered by EXP could combine with CP05 and EXP, and the binding efficiency of EXP with recovered exosomes was 95.9%, much higher than that of CP05 (76.8%).(F) detection of the binding efficiency of exosome in serum with CP05 and EXP, it's shown by the results that the capture efficiency of exosomes in serum by EXP was 93.5%, higher than 83.3% of CP05.

FIG. 6A shows that Nano sight was used to detect the particle size of exosomes in serum captured by CP05 and EXP.

FIG. 6B shows methods of CP05 and EXP capture and comparison of the number of exosomes in the equivalent ultra separated serum.

FIG. 6C shows that the morphology and size of exosomes captured by CP05 and EXP were detected by transmission electron microscopy.

FIG. 6D shows that Western blot was used to detect the marker protein capturing exosome.

FIG. 6E shows the binding efficiency of exosomes in serum with CP05 and EXP.

FIG. 6F shows a detection of the binding efficiency of exosome in serum with CP05 and EXP.

Figure 7:
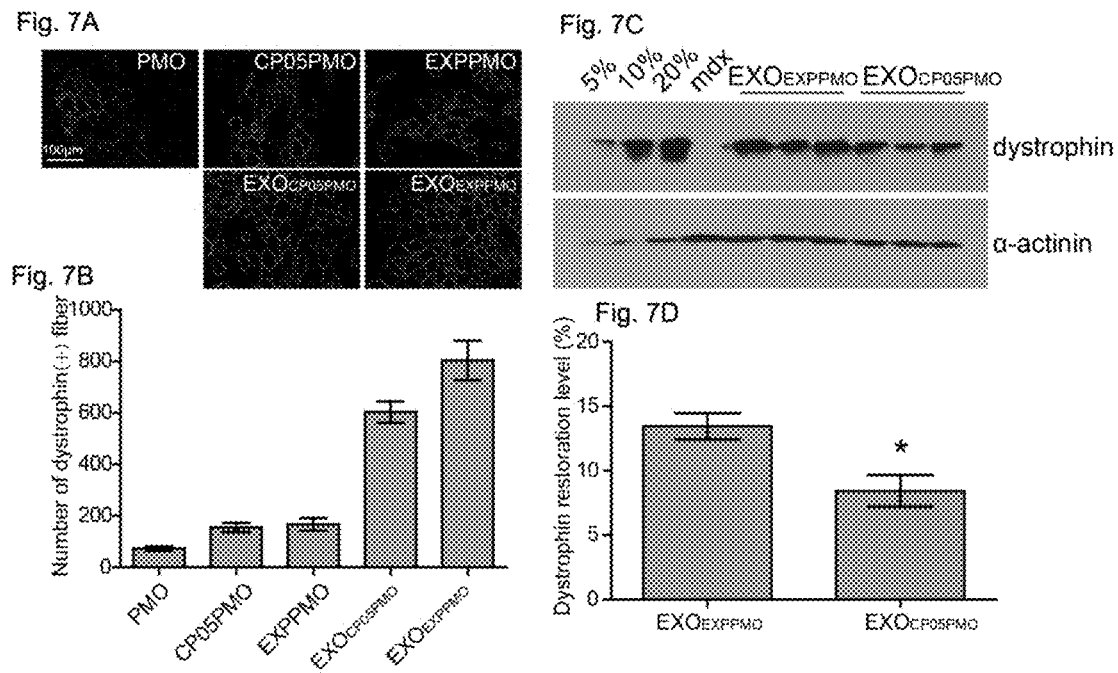

FIG. 7 shows functional evaluation of EXP-mediated exosomes as delivery vector. Antisense oligonucleotide drugs PMO were covalently conjugated to CP05 or EXP to form the peptide-PMO conjugatesCP05PMO and EXPPMO. CP05PMO and EXPPMO were co-incubated with exosomes to form EXOCP05PMO and EXOEXPPMO composition, in order to mediate in restoring the expression of dystrophin protein inmdx mousetibialis anterior (TA) muscles. Wherein, PMO means local injection of 2 μg PMO into tibialis anterior muscles; CP05PMO means local injection of 2 g CP05PMO into TA muscles; EXPPMO means local injection of 2 g EXPPMO into TA muscles; EXOCP05PMOmeans that 2 μg CP05PMO was co-incubated with 2 g exosomes and injected into TA muscles, EXOEXPPMO means that 2 g EXPPMO was co-incubated with 2 μg exosomes and injected into TA muscles. (A)immunohistochemistry was used to detect distribution of dystrophin-positive myofibersinmuscle fiber tissues. (B) Quantitative analysis on the number of dystrophin-positive myofibers after injection of different compounds in mdx mouse TA tissue. It's shown by the results that recovery of dystrophin myofibers of EXOEXPPMO group is higher than that of EXOCP05PMO group, which suggests that EXP can mediate high-efficient PMO delivery. (C) Western blot is used to detect and compare the recovery level of dystrophin protein after treated with EXOEXPPMO or EXOCP05PMO, wherein C57 means TA tissue protein of wild-type mouse, mdx means dystrophin deficient TA tissue protein without treat. (D) Quantitative analysis on recovery level of dystrophin protein treated with EXOEXPPMO or EXOCP05PMO. The results is consistent to immunohistochemistry and staining results, which showed higher levels of dystrophin expression in EXOEXPPMO treating group than EXOCP05PMO group.

FIG. 7A shows a distribution of dystrophin-positive myofibers in muscle fiber tissues.

FIG. 7B shows a quantitative analysis on the number of dystrophin-positive myofibers after injection of different compounds in mdx mouse TA tissue.

FIG. 7C shows a recovery level of dystrophin protein after treated with EXOEXPPMO or EXOCP05PMO.

FIG. 7D shows a quantitative analysis on recovery level of dystrophin protein treated with EXOEXPPMO or EXOCP05PMO.

Figure 8:
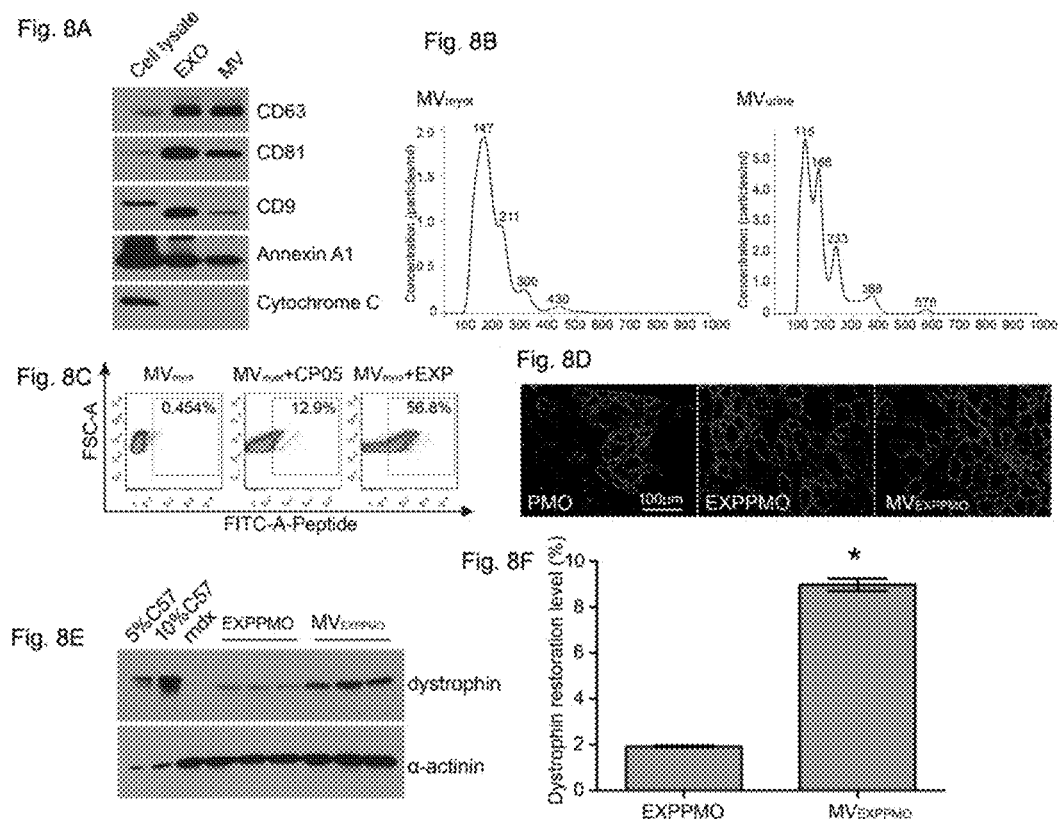

FIG. 8 shows functional test of EXP mediated MV (microcapsules) as drug delivery vectors. (A)Western blot is used to identify and compare the expression of biomarker proteins of MV and exosomes. It's shown by the results that Tetraspanin family proteins like CD81, CD9 and CD63 were expressed in MV, but mitochondrial marker protein Cytochrome C was not expressed. (B) particle size distribution of MV from different sources were detected by Nanosight. MVmyot means microvesicles derived from differentiated muscle cells; MVurine means microvesicles derived from urine. (C) Examination of the binding efficiency of EXP and CP05 to MVmyo was detected by flow cytometer. It's shown by the results that the binding efficiency of EXP to MVmyotis significantly higher than that of CP05. (D) shows local test of PMO drug delivered by EXP mediated MV in tibialis anterior muscles, and recovery of dystrophin positive muscle fiber was detected by immunohistochemical staining. (E)Western blot was used to detect the recovery of dystrophin protein expression after MVEXPPMO treatment. (F) shows quantitative analysis of dystrophin protein after treated with MVEXPPMO.

FIG. 8A shows a expression of biomarker proteins of MV and exosomes.

FIG. 8B shows a particle size distribution of MV from different sources.

FIG. 8C shows a binding efficiency of EXP and CP05 to MVmyo.

FIG. 8D shows a local test of PMO drug delivered by EXP mediated MV in tibialis anterior muscles, and recovery of dystrophin positive muscle fiber.

FIG. 8E shows a recovery of dystrophin protein expression after MVEXPPMO treatment.

FIG. 8F shows a quantitative analysis of dystrophin protein after treated with MVEXPPMO.

Figure 9:
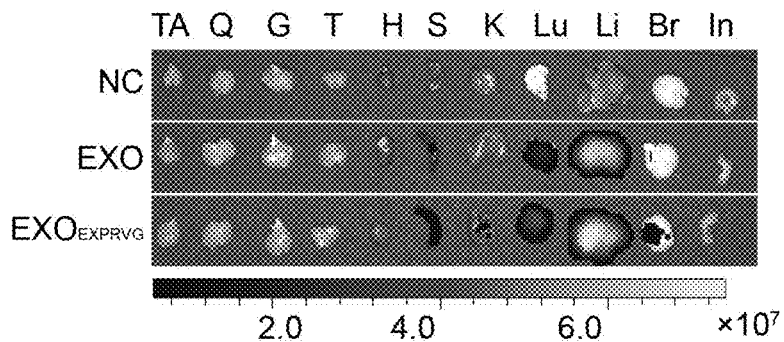

FIG. 9 shows the targeted transport of exosomes delivered by EXP mediated brain target peptide RVG. TA—tibialis anterior muscle; Q—quadriceps; G—gastrocnemius; T—triceps; H—heart; S—spleen; K—kidney; Lu—lung; Li—liver; Br—brain; In—small intestine.

EMBODIMENTS

The present invention will be further illustrated with the following figures and specific examples, but the protection scope is not limited by these examples. Unless otherwise specified, the experimental procedures in which the specific conditions are not indicated in the following examples are generally carried out according to routine procedures, or conditions which can be inferred by those skilled in the art within the knowledge range, or according to the conditions recommended by the manufacturer. The reagents and apparatus referred to in the following examples are typically commercially available products, or products that can be obtained by other publicly available means.

Description of the main apparatus involved in the following examples:

| Instrument name | Company/country |
| --- | --- |
| Flow cytometry | BD FACS ArialII/USA |
| Ultra clean bench | Airtech/China |
| high speed refrigerated centrifuge | Eppendorf/Germany |

| Instrument name | Company/country |
|---|---|
| Electric Heating constant Temperature Incubator | Tianjin Zhonghuan Experimental Electric Furnace Company limited./China |
| High pressure steam sterilizer | Sanyo company/Japan |
| Positive fluorescence microscope | Olympus BX51/Japan |
| Inverted fluorescence microscope | Olympus IX71/Japan |
| Confocal fluorescence microscope | Olympus Corporation/Japan |
| Automatic microplate reader | Bio-Tek Synergy HT/USA |
| −80° C. low temperature refrigerator | Sanyo company/Japan |
| −20° C. low temperature refrigerator | Haier Company/China |
| Ice maker | Grant company/United States |
| Micronuclei acid analyzer | NanoDrop 2000c/United States |
| Vertical Gel Tank | Bio-Rad/United States |

The $1^{st}$ group of examples: The polypeptide EXP of the invention.

This group of examples provides a polypeptide EXP, characterized in that, its amino acid sequence is set forth in SEQ ID NO. 1.

The $2^{nd}$ group of examples: The drug delivery system of the invention.

This group of examples provides a drug delivery system, characterized in that, comprises the polypeptide EXP according to any of the $1^{st}$ group of examples and drug delivery vector.

In some examples, the polypeptide EXP binds to drug delivery vector via CD63 and/or CD81 site.

Preferably, the drug delivery vector is vector that can express and carry CD63 and/or CD81;

Preferably, the drug delivery vector can express or carry CD63 and/or CD81 is selected from exosome, extracellular microvesicle, liposome, nanoparticle, and/or, exosome, extracellular microvesicle attaching CD63 and/or CD81 protein.

In other examples, the drug delivery system also includes: pharmacodynamically active molecule; the pharmacodynamically active molecule is selected from polypeptide, nucleic acid, and small molecule compound that can covalently connect with EXP.

Preferably, the polypeptide that can covalently connect with EXP is selected from muscle-targeting peptide-M12, liver cancer-targeting peptide-P47, cranial nerve-targeting peptide-RVG and other functional polypeptide, for example, NIND.

Preferably, the small molecule compound that can covalently connect with EXP is selected from Phosphorodiamidate Morpholino Oligomer (PMO).

Preferably, the nucleic acid that can covalently connect with EXP is selected from neutral, uncharged PMO or PNA.

The polypeptide that can covalently connect with EXP can also be a targeting peptide targeting different tissues, or a functional polypeptide of any sequence. Since peptide synthesis is a very mature technology, EXP is also a kind of peptide, which can be artificially synthesized with any other peptide, and any polypeptide can be synthesized with EXP. This is also the advantage of EXP, which can be synthesized with any sequence of polypeptide through mature artificial polypeptide synthesis technology.

The $3^{rd}$ group of examples: The targeted drug delivery system of the invention.

The present group of examples provides a targeted drug delivery system, characterized in that, comprises the polypeptide EXP according to any of the $1^{st}$ group of examples, drug delivery vector and targeting peptide.

In some embodiments, the polypeptide EXP binds to drug delivery vector via CD63 and/or CD81 site.

Preferably, the drug delivery vector is vector that can express or carry CD63 and/or CD81; the vector that can express or carry CD63 and/or CD81 is selected from exosome, extracellular microvesicle, liposome and nanoparticle, exosome, extracellular microvesicle attaching CD63 and/or CD81 protein.

In further embodiments, said targeted drug delivery system also includes:
pharmadynamically active molecule; the pharmadynamically active molecule is selected from polypeptide and nucleic acid molecule that can covalently connect with EXP;

Preferably, the polypeptide that can covalently connect with EXP is selected from M12, P47, RVG or NIND.

Preferably, the nucleic acid molecule that can covalently connect with EXP is selected from Phosphorodiamidate Morpholino Oligomer (PMO).

The $4^{th}$ group of examples: the enhanced drug delivery vector of the invention.

This group of embodiments provides the enhanced drug delivery vector, characterized in that, is drug delivery vector that is linked or modified by the polypeptide EXP according to any of the $1^{st}$ group of examples.

In some embodiments, the polypeptide EXP binds to the drug delivery vector via CD63 and/or CD81 site.

Preferably, the drug delivery vector is vector that can express or carry CD63 and/or CD81; the vector that can express or carry CD63 and/or CD81 is selected from exosome, extracellular microvesicle, plasmid that can express CD63 and/or CD81.

The $5^{th}$ group examples: a transport enhanced drug of the invention.

This group of embodiments provides a transport enhanced drug, characterized in that, the effective component of the drug is loaded on the enhanced drug delivery vector according to any of the $4^{th}$ group of examples.

For example, the nucleotide sequence of a specific polypeptide drug HMGN1 and the nucleotide sequence of EXP can be loaded into the gene expression vector (e.g., lentiviral vector: pCDH-CMVpuro-insulin-HMGN1). The polypeptide of HMGN1 and EXP can be expressed through said gene expression vector and binded to CD63/CD81 on drug delivery vector via EXP to form the structure of polypeptide+EXP+drug, i.e., Thus the polypeptide transport enhanced drug can be obtained.

For short peptide less than 60 amino acids, no gene expression system is needed; for peptides or proteins larger than 60 amino acids, gene expression vectors are needed.

In other embodiments, nucleic acid drug PMO can be covalently conjugated with EXP to obtain a complex structure PMO-EXP of nucleic acid drug, subsequently PMO-EXP can bind to CD63 and/or CD81 on drug delivery vector via EXP to generate a structure of PMO-EXP-drug delivery vector, namely, nucleic acid transport enhanced drug is obtained.

The 6$^{th}$ group of examples: a targeted drug of the invention.

This group of embodiments provides a targeted drug, characterized in that, the drug composition of the targeted drug is included in the targeted drug delivery system according to any of the 3$^{rd}$ group of examples.

For example, PMO covalently conjugated to EXP can be used for treating DMD.

The 7$^{th}$ group of examples: An extracellular vesicle recovery kit of the invention.

This group of embodiments provides a extracellular vesicle recovery kits characterized in that, comprises the polypeptide EXP according to any of the 1$^{st}$ group of examples.

In further embodiments, said extracellular vesicle recovery kit also includes conventional reagent for recovering and purifying extracellular vesicle.

Preferably, said conventional reagent for recovering and purifying extracellular vesicle includes:

More preferably, the polypeptide EXP is coated on nickel bead, or magnetic bead, or covalently linked to microsphere or nanobead by mature chemical processing.

In some embodiments, the extracellular vesicle is selected from exosome and/or microvesicle.

The 8$^{th}$ group of examples: A disease diagnosis kit of the invention

This group of embodiments provides a disease diagnosis kit, characterized in that, the disease diagnosis markers are exosome surface protein molecule and disease-related specific protein molecule, such as liver cancer specific antigen AFP; the kit includes the polypeptide EXP according to any of the 1$^{st}$ group of examples.

For example, for the diagnosis of tumor or muscle dystrophic patients, just like CP05 in the prior art, EXP can be adhered to the magnetic bead to capture free exosome, and whether suffering from the disease can be diagnosed by detect concentration of exosome.

In further embodiments, said diagnostic kit also comprises reagent for recovering and purifying exosome.

Preferably, the reagent for purifying exosome includes: nickel bead coated with polypeptide EXP; binding buffer of pH7.4 with a formula of 50 mM imidazole, 500 mM sodium chloride, 20 mM disodium hydrogen phosphate; washing solution of pH7.4 with a formula of 75 mM imidazole, 500 mM sodium chloride, 20 mM disodium hydrogen phosphate; eluent of pH7.4 with the formula of 500 mM imidazole, 500 mM sodium chloride, 20 mM disodium hydrogen phosphate; all above reagents are commercially available.

Preferably, the exosome is selected from exosome from human serum, and/or exosome from human urine, and/or free exosome from other source, and/or exosome from cell culture supernatant.

The 9$^{th}$ group of examples: a method for purifying extracellular vesicle of the invention.

This group of embodiments provides a method for purifying extracellular vesicle, characterized in that, comprises binding or capturing the extracellular vesicle with the polypeptide EXP according to any of the 1$^{st}$ group of examples.

In further embodiments, the method for purifying microvesicles also includes:

Step 1: His labeled EXP and CP05 (100 μg) were combined with 40 L nickel beads in 200 μL binding solution at 4° C. for 1 h under rotation.

Step 2: 1 mL of pre-centrifuged serum (4400 g, centrifugation for 20 min; 13000 g, centrifugation for 5 min) was added to the nickel beads coated with His-EXP and His-CP05, and was incubated at 4° C. for 30 min under rotation.

Step 3: discarding the serum and washing off non-specific binding with the washing buffer for 3 times (10 min each time).

Step 4: adding 100 L of the elution buffer to recover the extracellular vesicle.

In some embodiments, the extracellular vesicle is selected from exosome and/or microvesicle.

The 10$^{th}$ group of examples: Use of the polypeptide EXP in pharmacy.

This group of embodiments provides use of said polypeptide EXP according to any of the 1$^{st}$ group of examples in pharmacy.

In specific embodiments, the use includes that said polypeptide EXP is connected with the drug delivery vector to obtain the enhanced drug delivery vector based on the polypeptide EXP-vector complex.

In further embodiments, said use also includes: the drug molecule is connected with the EXP-vector complex to obtain the drug based on the drugs molecule-EXP-vector complex.

In some further embodiments, said use also includes: targeting peptide is further connected with the drug molecule-EXP-vector complex to obtain targeted drug.

The 11$^{th}$ group of examples: use of the polypeptide EXP in manufacturing disease diagnostic reagent in the present invention This group of embodiments provides use of the polypeptide EXP of any of the 1$^{st}$ group of examples in manufacturing disease diagnostic reagent.

In specific embodiments, the application includes: the polypeptide EXP is connected with the exosome.

In some embodiments, said exosome is derived from human serum, human urine, or other source.

Experimental Example 1: Flow cytometry assay was used to detect the binding capacity of EXP and other peptides to exosome.

1.1 Flow cytometry is used to detect the binding capacity of EXP and other peptides to exosome.
(1) FAM-labeled CP05 and other peptides respectively with amount of 0.06 g were mixed with exosome from different source like dC2C12, CDC and serum respectively with amount of 10 g, and DPBS is used to make up a deficiency to 200 μl in volume with.
(2) The mixture prepared as described in (1) was incubated at 4° C. for 2-4 hrs under rotation in vertical shaker.
(3) the binding efficiency was detected with flow cytometry.

Figure 1:
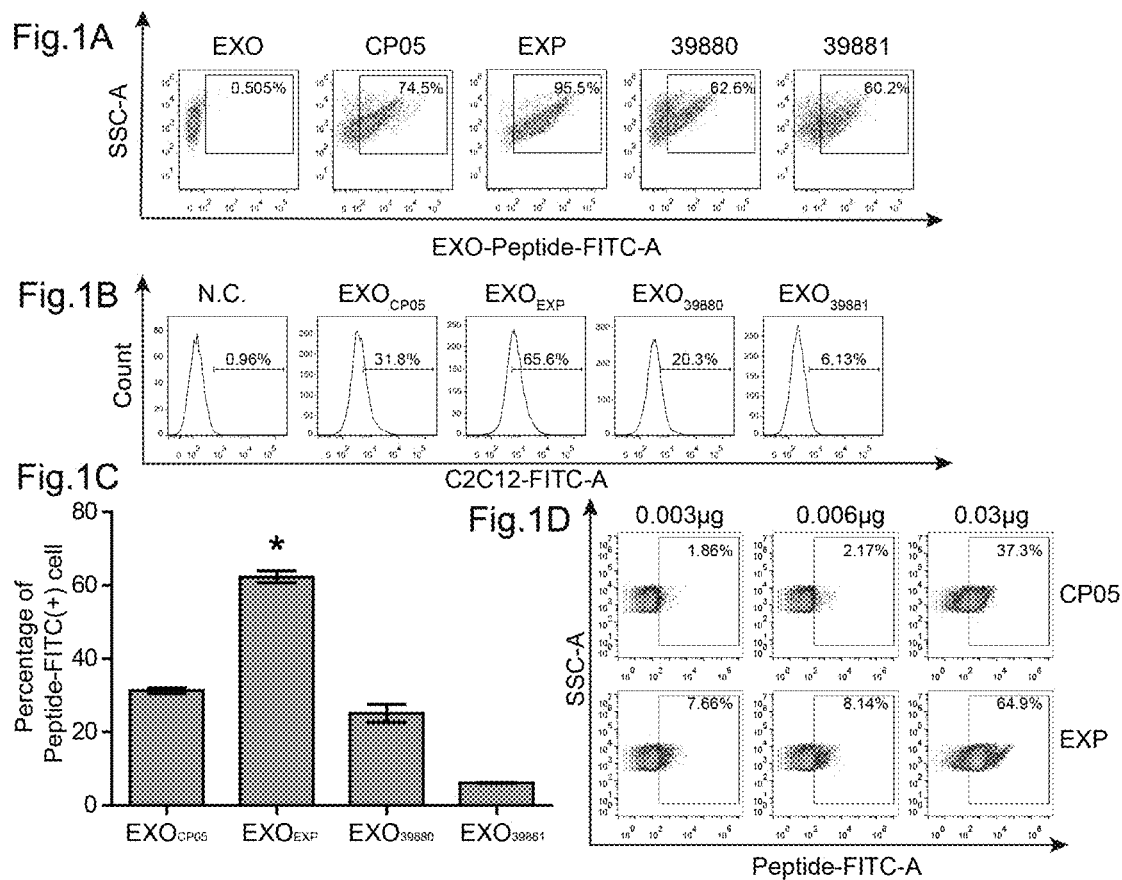
FIG. 1 shows the binding efficiency of anchoring polypeptide with exosome. The present invention shows three polypeptides with different sequences, EXP (CRHKMWTVKSRL), 39880(CKHNQWTVTSRL) and 39881 (SQCSVSTKL). The FAM-labeled peptides EXP, CP05, 39880, 39881 were respectively co-incubated with exosome from differentiated muscle cells C2C12(dC2C12), and the binding efficiency of different polypeptides with exosome was detected by flow cytometry.

The results were shown in FIG. 1 (A).

1.2 Detection on the capacity entering cells of exosome-mediated CP05 and other peptides.
(1) C2C12 cells were digested, counted and seeded into 24-well plates (4×10$^4$/well) and grown at 5% $CO_2$ at 37° C. for 12 hrs.
(2) FAM-labeled CP05 and other peptides were incubated for 4 hrs as described in 1.1.
(3) the incubated $EXO_{EXP}$ and $EXO_{CP05}$ were respectively added into C2C12 cells and incubated in serum-free DMEM medium for another 24 hrs by changing medium.

(4) Dead cells and fluorescent molecule non-specifically bound to the surface of cells were washed off with DPBS 24 hrs later.
(5) Cells were digested with 0.25% trypsin.
(6) centrifugation was performed at 1000 rpm for 5 min and the supernatant was discarded.
(7) Cell precipitates were re-suspended with 500 μl DPBS.
(8) centrifugation was performed at 1000 rpm for 5 min and the cell precipitates were washed twice.
(9) Cell precipitates were resuspended with 200 W DPBS.
(10) the percentage of FITC-positive cells after adding $EXO_{CP05}$ and $EXO_{EXP}$ was analyzed by Flow cytometry.

The results were shown in FIGS. 1 (B) and (C).

Experimental example 2: Detection of the binding stability of EXP and CP05 to exosome.
(1) C2C12 cells were digested, counted and seeded into 24-well plates ($4\times10^4$/well) and grown at 37° C. under 5% $CO_2$ for 12 hrs.
(2) FAM-labeled EXP and CP05 (20 μg) were respectively incubated with DiI-labeled exosomes (10 μg) at 4° C. for 4 hrs under rotation.
(3) The incubated $EXO_{EXP}$ and $EXO_{CP05}$ respectively were added into C2C12 cells and after changing medium, cells were cultured in serum-free DMEM medium at 37° C.
(4) after being cultured for different time (6 hrs, 12 hrs, 24 hrs, 48 hrs), cells were washed by DPBS.
(5) Cells were fixed with 4% paraformaldehyde at room temperature for 30 min, and were mounted.
(6) The co-localization efficiency of exosome (DiI) and polypeptide (FAM) and fluorescence energy transfer at different time-points were observed with confocal microscopy.

The results were shown in FIG. 2.

Experimental example 3: Evaluation of competitive binding capacity of exosome between EXP andCP05.
(1) AF750-labeled CP05 (0.06 g) was respectively incubated with FAM-labeled CP05 (0.06 g, 0.3 μg) or FAM-labeled EXP (0.06 g, 0.3 g) and exosome (10 μg), and DPBS was used to make up a deficiency to 200 μl.
(2) Incubated for 4 hrs at 4° C. under rotation.
(3) Flow cytometry was used to examine the percentage of FITC- and APC-positive exosomes.

The results were shown in FIG. 3.

Experimental example 4: Validation of EXP target detection.
(1) 100 g EXP or 100 μg CP05 were respectively mixed with 30 μlactivated magnetic beads and incubated overnight at 4° C.
(2) The magnetic beads were recovered after washing off polypeptides that were unbound to magnetic beads with PBST.
(3) C2C12 cells were lysed with non-denatured tissue lysis buffer for 30 min on ice and centrifuged at 12000 rpm to recover supernatant.
(4) The supernatant of C2C12 lysis was added to the recovered magnetic beads and incubated for 2 hrs at 4° C.
(5) The supernatant was discarded and the precipitates were washed with PBST under rotation for 3 times (5 min each time) to wash off the nonspecific binding protein, and then PBST was discarded.
(6) 1× loading buffer (100 μl) was added into the precipitates and 50 μl sample was loaded into SDS-PAGE gels.
(7) The gels were stained with silver dyes or transferred to membrane and hybridized with CD63, CD9, CD81, CD82 antibodies.

The results were shown in FIG. 4.

Experimental example 5: Comparison on binding efficiency of EXP and exosomes from different sources.
(1) 0.06 μg FAM-labeled CP05 and 0.06 μg of different peptides were respectively mixed with 10 μg exosome from dC2C12, CDC, serum, and DPBS was used to make up a deficiency to 200 μl.
(2) The mixture was incubated for 2-4 hrs at 4° C. under rotation in vertical shaker.
(3) The binding efficiency was detected with flow cytometry.

The results were shown in FIG. 5.

Experimental example 6: Characterization and functional validation of exosome captured from serum by EXP.
(1) His-tagged EXP and CP05 (100 μg) were respectively mixed with 40 nickel beads in 200 μl binding solution at 4° C. for 1 h under rotation.
(2) 1 ml pre-centrifuged serum was added to His-EXP and His-CP05 coated nickel beads (centrifuged at 4400 g for 20 min, followed by 13000 g for 5 min), and then incubated at 4° C. for 30 min;
(3) The serum was discarded and the nonspecific binding was washed with the washing solution for 3 times, 10 min each time.
(4) 100 eluent was used to recover extracellular vesicles.

6.1 Measurement of the size of captured exosomes.
(1) 20 W of exosomes recovered from elution were diluted into 1 ml of PBS.
(2) Nanosight was used to detect the size distribution of captured exosomes.

The results were shown in FIGS. 6 (A) and (B).

6.2 Morphological identification of captured exosomes.
(1) $10^1$ of recovered exosomes by elution and 10 μl of recovered exosomes by ultra-centrifugation were added with the same volume of 4% PFA for fixing.
(2) 10 μl exosomes fixing solution were absorbed onto the copper mesh for 20 min at room temperature.
(3) 100 PBS was dropped on the sealing membrane, with the copper mesh facing down, and unfixed exosomes on the copper mesh were washed off.
(4) For fixation, the copper mesh was transferred to 1% glutaraldehyde for 5 min.
(5) 100 μl $H_2O$ was dropped on the sealing membrane with the copper mesh facing down, and the copper mesh was washed for 8 times, 2 min each time.
(6) Transfer the copper mesh to 501 uranium oxalate solution (pH=7) and stain for 5 min.
(7) the copper mesh was transferred to 50 μl methylcellulose—uranium oxalate on ice for 10 min.
(8) the copper mesh was taken out of methylcellulose—uranium oxalate and dried in air after drawing redundant liquid.
(9) the morphology of exosomes was observed with transmission electron microscopy.

The results were shown in FIG. 6C.

6.3 Detection on protein expression of captured exosomes.
(1) 5× loading buffer was added to 30 μl exosomes recovered by elution and 10 μg exosomes recovered by ultracentrifugation, and denatured at 100° C.
(2) The samples were loaded onto 10% SDS-PAGE and run for 1.5 hrs.
(3) protein transfer onto membrane at 250 mA for 2.5 hrs.
(4) the membrane was blocked for 2 hrs at 4° C.

(5) the primary antibodies (CD63, CD81, CD9, HSC90, Alix) were added and incubated overnight.
(6) the membrane was washed for 3 times with PBST, 10 min each time.
(7) the secondary antibody was incubated with the membrane for 2 hrs at 4° C.
(8) the membrane was washed with PBST for 3 times, 15 min each time.
(9) the membrane was developed.

The results were shown in FIG. 6 (D).

Experimental example 7: Exp mediated the functional test of exosomes transporting PMO.

7.1 Immunohistochemical staining of muscle tissues.
(1) anterior muscles (TA) of treated mdx mice was cut into 8-μm thick sections by freezing microtome;
(2) the sections was soaked in PBS for 15 min, blocking buffer containing 20% fetal bovine serum (FBS) and 20% goat serum (NGS) was added for blocking for 1 hour;
(3) the blocking buffer was discarded and dystrophin primary antibody (1:3000) was added for incubating for 2 hrs;
(4) the sections were washed with PBS for 3 times, and the fluorophore-labeled secondary antibody was added and incubated for 1 hr;
(5) the sections were washed with PBS for 3 times, mounted, dried in air and observed through the fluorescence microscope.

The results were shown in FIG. 7 (A).

7.2 Western Blot Staining
(1) 5× loading buffer was added to 50 g different muscle samples and boiled at 72° C. for 5 min.
(2) the samples were loaded onto 4-6% SDS-PAGE gel and run for 2.5 hrs.
(3) proteins onto the membrane was transferred at 110 mA for 18 hrs.
(4) the membrane was blocked for 2 hrs at 4° C.
(5) the primary antibodies (dystrophin and α-actinin) was incubated with the membrane overnight.
(6) the membrane was washed with PBST for 3 times, 10 min each time.
(7) the membrane was incubated with secondary antibodies for 2 hrs at 4° C.
(8) the membrane was washed with PBST for 3 times, 15 min each time.
(9) the membrane was developed.

The results were shown in FIG. 7 (C).

Example 8: Functional Evaluation on MV Mediated by EXP as Drug Delivery Vector 8.1 The procedures for MV recovery.
(1) the cell supernatant or urine was balanced and centrifuged at 4500 g for 20 min at 4° C.
(2) the supernatant was collected with precipitate discarded and centrifuged at 13000 g for 5 min at 4° C.
(3) the supernatant was collected with precipitate discarded and centrifuged at 20000 g for 90 min at 4° C.
(4) the supernatant was discarded and the precipitate was resuspended with 1 ml PBS, and centrifuged at 20000 g for 90 min at 4° C.
(5) the supernatant was discarded and the precipitate was resuspended with 100l of PBS.
(6) Western Blot was used to detect the expression of biomarker protein, and nanosight was used to detect the size distribution of particles, their procedures were as above.

The results were shown in FIG. 8 (A), 8(B).

The invention claimed is:

1. A polypeptide EXP, comprising the amino acid sequence of SEQ ID NO: 1.

2. A drug delivery system product, comprising the polypeptide EXP according to claim 1 and a drug delivery vector.

3. The drug delivery system product according to claim 2, comprising the polypeptide EXP binding to the drug delivery vector via CD63 and/or CD81 wherein the drug delivery vector is selected from the group consisting of exosome and extracellular microvesicle.

4. The drug delivery system product according to claim 2, further comprising a pharmacodynamically active molecule; said pharmacodynamically active molecule is selected from the group consisting of polypeptide, polynucleotide, and a small molecular compound which is covalently conjugated to the polypeptide EXP; wherein the polypeptide which is covalently conjugated to the polypeptide EXP is selected from the group consisting of muscle-targeting peptide M12, liver cancer-targeting peptide P47, brain-targeting peptide RVG and N1ND; wherein the polynucleotide which is covalently conjugated to the polypeptide EXP is neutral, uncharged PNA; or wherein the small molecule compound which is covalently conjugated to the polypeptide EXP is phosphorodiamidate morpholino oligomer (PMO).

5. A targeted drug delivery system product, comprising the polypeptide EXP according to claim 1, a drug delivery vector and a targeting peptide.

6. The targeted drug delivery system product according to claim 5, comprising the polypeptide EXP binding to the drug delivery vector via CD63 and/or CD81 wherein the drug delivery vector is selected from the group consisting of exosome and extracellular microvesicle.

7. A targeted drug, comprising a drug composition wherein the drug composition is included in the targeted drug delivery system product of claim 6.

8. The targeted drug delivery system product according to claim 5, further comprising a pharmacodynamically active molecule; said pharmacodynamically active molecule is selected from the group consisting of polypeptide and polynucleotide which is covalently conjugated to the polypeptide EXP; wherein the polypeptide which is covalently conjugated to the polypeptide EXP is selected from the group consisting of muscle-targeting peptide M12, liver cancer-targeting peptide P47, brain-targeting peptide RVG and N1ND or wherein the polynucleotide which is covalently conjugated to the polypeptide EXP is neutral, uncharged PNA.

9. An enhanced drug delivery vector, comprising a drug delivery vector and the polypeptide EXP according to claim 1 wherein the drug delivery vector is linked or modified by the polypeptide EXP.

10. The enhanced drug delivery vector according to claim 9, comprising the polypeptide EXP binding to the drug delivery vector via CD63 and/or CD81 wherein the drug delivery vector is selected from the group consisting of exosome and extracellular microvesicle.

11. A drug with enhanced delivery, comprising a drug loaded on the enhanced drug delivery vector of claim 9.

12. An extracellular vesicle extraction kit product, comprising the polypeptide EXP according to claim 1 and a reagent for extracting and purifying an extracellular vesicle.

13. The extracellular vesicle extraction kit product according to claim 12, wherein the polypeptide EXP is coated on a nickel bead or a magnetic bead or covalently linked to a microsphere or nanobead by mature chemical processing.

14. A disease diagnosis kit, comprising a disease diagnosis marker and the polypeptide EXP according to claim 1 wherein the disease diagnosis marker is an exosome surface protein molecule, a disease-related specific protein molecule, or liver cancer specific antigen AFP.

15. The disease diagnosis kit according to claim 14, further comprising a reagent for extracting and purifying an exosome.

16. The disease diagnosis kit according to claim 15, the reagent for extracting and purifying the exosome includes: a nickel bead coated with the polypeptide EXP; a binding buffer of pH 7.4 comprising 50 mM imidazole, 500 mM sodium chloride, and 20 mM disodium hydrogen phosphate; a washing solution of pH 7.4 comprising 75 mM imidazole, 500 mM sodium chloride, and 20 mM disodiumhydrogen phosphate; and an eluent of pH 7.4 comprising 500 mM imidazole, 500 mM sodium chloride, and 20 mM disodium hydrogen phosphate wherein the exosome is selected from the group consisting of a free exosome derived from a source other than a cell culture supernatant and a free exosome derived from a cell culture supernatant.

17. A method for purifying extracellular vesicle, comprising step 1, binding or capturing an extracellular vesicle with the polypeptide EXP according to claim 1.

18. The method for purifying extracellular vesicle according to claim 17, comprising step 2, combining the polypeptide EXP labeled with His with 100 μg CP05 and 40 μl nickel bead in 200 μl binding buffer and incubating for 1 h at 4° C.; step 3, coating a nickel bead with the polypeptide EXP labeled with His, adding a His-CP05 to 1 ml pre-centrifuged serum and incubating at 4° C. for 30 min; step 4, discarding the serum and washing off any nonspecifically bound molecules with a washing solution three times for 10 min each; and step 5, utilizing 100 μl eluent to extract the extracellular vesicle.

19. The method for purifying extracellular vesicle according to claim 17, wherein an extracellular vesicle is selected from the group consisting of exosome and microvesicle.

20. A method for manufacturing pharmaceuticals, comprising step 1, utilizing the polypeptide EXP according to claim 1 to manufacture pharmaceuticals.

21. The method for manufacturing pharmaceuticals according to claim 20, further comprising step 2, connecting the polypeptide EXP with a drug delivery vector to obtain an enhanced drug delivery vector based on the polypeptide EXP and the drug delivery vector complex.

22. The method for manufacturing pharmaceuticals according to claim 21, further comprising connecting a drug molecule with the polypeptide EXP-drug delivery vector complex thereby obtaining a drug based on the drug molecule and polypeptide EXP-drug delivery vector complex.

23. The method for manufacturing pharmaceuticals according to claim 22, further comprising step 4, connecting a targeting peptide with the drug molecule-polypeptide EXP-drug delivery vector complex thereby obtaining a targeted drug.

24. A method for preparing a disease diagnosis reagent, comprising step 1 utilizing the polypeptide EXP according to claim 1 to prepare a disease diagnosis reagent.

25. A method for preparing a disease diagnosis reagent according to claim 24, comprising step 2 connecting the polypeptide EXP to an exosome.

26. A method for preparing a disease diagnosis reagent according to claim 25, wherein the exosome is selected from the group consisting of exosomes derived from human serum and exosomes derived from human urine.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: EXP

<400> SEQUENCE: 1

Cys Arg His Lys Met Trp Thr Val Lys Ser Arg Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: 39880

<400> SEQUENCE: 2

Cys Lys His Asn Gln Trp Thr Val Thr Ser Arg Leu
1               5                   10

<210> SEQ ID NO 3
<211> LENGTH: 9
<212> TYPE: PRT
<213> ORGANISM: Artificial Sequence
<220> FEATURE:
<223> OTHER INFORMATION: 39881
```

```
<400> SEQUENCE: 3

Ser Gln Cys Ser Val Ser Thr Lys Leu
1               5
```